(12) United States Patent
Lin et al.

(10) Patent No.: US 8,193,396 B2
(45) Date of Patent: Jun. 5, 2012

(54) PROCESS FOR PRODUCING ALLYL ALCOHOL

(75) Inventors: Shaw-Chan Lin, West Chester, PA (US);
Lawrence M. Candela, Havertown, PA (US); Andrew P. Kahn, Eagleville, PA (US); Elizabeth I. Ross-Medgaarden, West Grove, PA (US); Gary A. Sawyer, Media, PA (US)

(73) Assignee: Lyondell Chemical Technology, L.P., Houston, TX (US)

( * ) Notice: Subject to any disclaimer, the term of this patent is extended or adjusted under 35 U.S.C. 154(b) by 294 days.

(21) Appl. No.: 12/660,372

(22) Filed: Feb. 25, 2010

(65) Prior Publication Data

US 2011/0207973 A1      Aug. 25, 2011

(51) Int. Cl.
*C07C 27/00* (2006.01)
*C07C 27/02* (2006.01)
*C07C 27/14* (2006.01)

(52) U.S. Cl. ........................................ 568/877

(58) Field of Classification Search .................... 568/877
See application file for complete search history.

(56) References Cited

U.S. PATENT DOCUMENTS

| | | | |
|---|---|---|---|
| 3,925,452 A | 12/1975 | Swodenk et al. | |
| 3,970,713 A | 7/1976 | Scharfe et al. | |
| 4,409,396 A | 10/1983 | Dempf et al. | |
| 4,743,707 A | 5/1988 | Matsuhira | |
| 5,011,980 A | 4/1991 | Sano et al. | |
| 6,303,536 B1 | 10/2001 | Chen et al. | |
| 2006/0167307 A1 | 7/2006 | Saihata et al. | |
| 2006/0247462 A1 | 11/2006 | Saihata et al. | |
| 2009/0166174 A1 | 7/2009 | Maruta et al. | |

FOREIGN PATENT DOCUMENTS

| | | |
|---|---|---|
| JP | 53071009 A | 6/1978 |
| JP | 61-238745 A | 10/1986 |
| JP | 61238745 (A) | 10/1986 |
| JP | 1250338 A | 10/1989 |
| JP | 2096548 A | 4/1990 |

OTHER PUBLICATIONS

Fuchigami Y; Moriya S; & Tsurumaru N; High yield allyl alcohol preparation comprise acetate hydrolysis distil product, Database WPI 1-13 Week 198649, AN 1986-322227; Thomson Scientific, London, GB, (1986).

*Primary Examiner* — Brian J Davis

(57) ABSTRACT

A process for producing allyl alcohol is disclosed. The process comprises reacting propylene, acetic acid, and oxygen to produce a reaction mixture. The reaction mixture is distilled to produce a vapor stream comprising propylene and a liquid stream comprising allyl acetate, acetic acid, acrolein, and allyl diacetate. The liquid stream is distilled to produce a lights stream comprising acrolein; a side draw comprising allyl acetate, acetic acid, and water; and a bottoms stream comprising acetic acid and allyl diacetate. The bottoms stream is distilled to remove a heavies stream comprising allyl diacetate. The side draw is hydrolyzed to produce allyl alcohol.

13 Claims, 1 Drawing Sheet

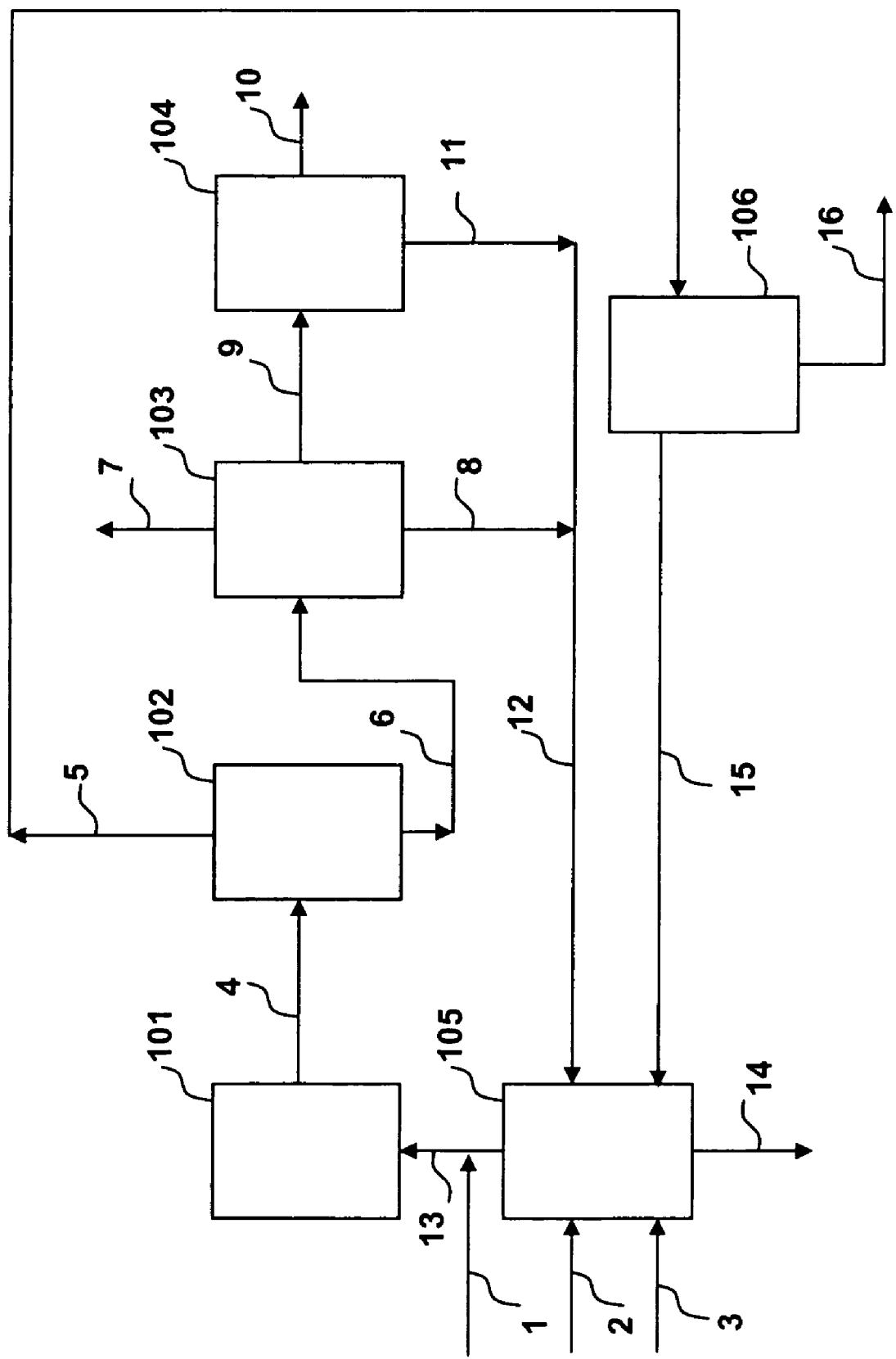

PROCESS FOR PRODUCING ALLYL ALCOHOL

FIELD OF THE INVENTION

This invention relates to a process for reacting propylene, acetic acid, and oxygen to produce allyl acetate and hydrolyzing the allyl acetate to produce allyl alcohol.

BACKGROUND OF THE INVENTION

Allyl alcohol is a valuable chemical intermediate. Allyl alcohol can be produced by acetoxylation of propylene, followed by hydrolysis of the resulting allyl acetate. Acetoxylation to produce allyl acetate can be performed by reacting propylene, acetic acid, and oxygen in the vapor phase in the presence of a palladium catalyst. The reaction mixture is typically separated into a vapor stream comprising propylene, oxygen, carbon dioxide, which is generally recycled to the acetoxylation reaction, and a liquid stream comprising allyl acetate, acetic acid, and water. However, the liquid stream tends to contain heavy impurities. One such impurity is allyl diacetate, also known as allylidene diacetate or 1,1-diacetoxy-2-propene. The heavy impurities, like allyl diacetate, can deactivate solid acid catalysts used in a subsequent step for hydrolyzing allyl acetate. A few publications have taught removing the allyl diacetate by decomposing it before the liquid stream is hydrolyzed. See, for example, Japanese Pat. Appl. Nos. 01-250338, 2-096548, 61-238745, and 53-071009. Also see co-pending application Ser. Nos. 12/322,650, filed Feb. 5, 2009 and 12/653,677, filed Dec. 17, 2009.

Co-pending application Ser. No. 12/322,650 describes a process for purifying an acetoxylation mixture containing allyl diacetate by contacting the mixture in a vapor phase with a solid acidic catalyst to convert the allyl diacetate to acrolein and removing the acrolein from the reaction product. Co-pending application Ser. No. 12/653,677 teaches a process for purifying allyl acetate by distilling an acetoxylation mixture at elevated pressure to remove propylene and generate a first bottoms mixture comprising allyl acetate, acetic acid, acrolein, allyl diacetate, and 3-acetoxypropionaldehyde. The first bottoms mixture is flash vaporized, and the resulting vapor is contacted with a solid acidic catalyst to decompose the allyl diacetate. The flashed product, which comprises allyl acetate, acetic acid, and acrolein, is distilled to remove acrolein and generate a second bottoms mixture comprising allyl acetate and acetic acid. The second bottoms mixture may be used to manufacture allyl alcohol.

There is a need in the industry to develop more economic processes wherein the heavy impurities such as allyl diacetate are removed by more efficient methods.

SUMMARY OF THE INVENTION

This invention is a process for producing allyl alcohol. The process comprises reacting propylene, acetic acid, and oxygen in the presence of a supported palladium catalyst to produce a reaction mixture. The reaction mixture is distilled to produce a vapor stream comprising propylene and a liquid stream comprising allyl acetate, acetic acid, acrolein, and allyl diacetate. The liquid stream is distilled to produce a lights stream comprising acrolein; a side draw comprising allyl acetate, acetic acid, and water; and a bottoms stream comprising allyl diacetate and acetic acid. The bottoms stream is distilled to remove a heavies stream comprising allyl diacetate. The side draw is hydrolyzed to produce allyl alcohol.

BRIEF DESCRIPTION OF DRAWING

FIG. 1 illustrates a process for producing allyl alcohol according to this invention.

DETAILED DESCRIPTION OF THE INVENTION

The process comprises reacting a feed comprising propylene, acetic acid, and oxygen (acetoxylation reaction). The acetoxylation reaction is generally performed in the presence of a palladium catalyst, preferably a supported palladium catalyst. The supported palladium catalyst generally comprises 0.1 to 5.0 wt %, preferably 0.3 to 1.5 wt % palladium. In addition, the catalyst may comprise a Group 11 element, i.e., gold, copper, silver, and mixtures thereof. The content of gold, copper, or silver may be in the range of 0 to 5.0 wt %, preferably in the range of 0.02 to 1.0 wt % of the supported catalyst.

The catalyst may additionally comprise an activator. An activator is an alkali or alkaline earth metal compound, examples of which are hydroxides, acetates, nitrates, carbonates, and bicarbonates of potassium, sodium, cesium, magnesium, barium, and the like. Potassium and cesium salts are preferred activators. The activator content may be in the range of 0 to 15 wt %, preferably 1.5 to 10 wt % of the supported catalyst.

The supported palladium catalyst comprises a carrier. Suitable carriers include alumina, silica, titania, carbon, and like, and mixtures thereof. Preferably, the carrier has a surface area of at least 1 $m^2/g$ and a pore volume of 0.1 to 1.5 mL/g.

The catalyst may be prepared by many techniques. Examples of these techniques are disclosed in U.S. Pat. Nos. 3,925,452, 5,011,980, 6,303,536, and U.S. Pat. Appl. Pub. Nos. 2006/0167307 and 2006/0247462.

In preparing the catalyst, the carrier can be simultaneously or successively impregnated with a palladium compound, optionally a Group 11 metal salt, and optionally an activator. Preferably, the impregnation is performed with aqueous solutions.

Suitable palladium compounds include palladium chloride, sodium chloropalladate, palladium nitrate, palladium sulfate, the like, and mixtures thereof. Suitable Group 11 metal salts include chlorides, nitrates, and sulfates. Examples are tetrachloroauric acid, sodium tetrachloroaurate, copper chloride, copper nitrate, copper sulfate, silver nitrate, the like, and mixtures thereof. Suitable activators include hydroxides, carbonates, bicarbonates, metasilicates of alkali and alkaline earth metals, the like, and mixtures thereof.

One method to impregnate the carrier involves contacting the carrier with an aqueous solution containing both a palladium compound and a Group 11 metal salt. In another method, the carrier is contacted with a palladium compound and a Group 11 metal salt in separate steps.

A fixing agent may be used in preparing the catalyst. Fixing agents help to bind the palladium compound and the Group 11 metal salts, if used, to the carrier. Suitable fixing agents include alkali metal, alkaline earth metal, or ammonium compounds, for example, their hydroxides, carbonates, bicarbonates, metasilicates, and the like, and mixtures thereof. A fixing agent may be contacted with the carrier during or after the carrier is impregnated with the palladium compound and optionally the Group 11 metal salt.

The impregnated carrier is usually calcined (heated at an elevated temperature) in a non-reducing atmosphere. Preferably, the calcination is carried out at a temperature in the range of 100 to 600° C., more preferably, in the range of 250 to 500° C. Suitable non-reducing gases for the calcination include helium, nitrogen, argon, oxygen, air, carbon dioxide, the like, and mixtures thereof. Preferably, the calcination is carried out in nitrogen, oxygen, air, or mixtures thereof.

Following the calcination, the resulting material is normally reduced so that at least a portion of the palladium and the Group 11 metal, if used, is converted to their corresponding elements of zero valences. The reduction is performed by contacting it with a reducing agent. Suitable reducing agents include hydrogen, carbon monoxide, olefins, aldehydes, alcohols, hydrazines, the like, and mixtures thereof. Temperatures employed for the reduction are in the range of 20 to 700° C. Hydrogen gas is a preferred reducing agent. Generally, a gas mixture containing hydrogen and another gas such as argon, helium, nitrogen, or the like, is used. The reduction temperature is preferably in the range of 300 to 700° C., more preferably, in the range of 450 to 550° C.

The feed to the acetoxylation reaction comprises propylene. The concentration of propylene in the feed is generally between 20 to 80 mol %, preferably 40 to 70 mol %. The feed to the reactor includes all streams entering the reactor, including fresh propylene, fresh oxygen, fresh acetic acid, and recycled streams. A propylene content of greater than 50 mol % is particularly desirable. Commercially available polymer grade propylene and chemical grade propylene are suitable sources of propylene. The source of propylene preferably has a purity of at least 90 mol %, most preferably, at least 94 mol %.

The feed comprises acetic acid. The concentration of acetic acid in the feed typically is 8 to 25 mol %, preferably 10 to 18 mol %.

The feed comprises oxygen. The concentration of oxygen in the feed is typically 1 to 8 mol %, preferably 2 to 6 mol %. The oxygen may be supplied to the process in the form of a mixture with an inert gas such as nitrogen. Air may be used. The oxygen source used for the process preferably has a purity of at least 90 mol %, more preferably at least 95 mol %. The allowed oxygen concentration in the feed is determined by the flammability limit. The flammability limit of the feed depends on the temperature, the pressure, and its composition.

The feed may comprise a diluent. A diluent helps to prevent formation of an explosive mixture in the reactor and control the temperature rise. Examples of suitable diluents include propane, nitrogen, helium, argon, the like, and mixtures thereof.

The feed may comprise water. The concentration of water in the feed is typically from 0 to 15 mol %, more preferably from 5 to 10 mol %.

The reaction may be performed in a fixed-bed reactor or a fluidized-bed reactor, or the like. A fixed-bed reactor is preferred. In one example, a multitubular fixed-bed reactor is used. Typically the tube diameter is from 1 to 4 inches (U.S. Pat. No. 3,970,713).

The feed is gaseous under the reaction conditions. Accordingly, the quantities of acetic acid and water entering the reactor are adjusted so that the feed is in the gas phase under the temperature and pressure selected for the reaction. The reaction is generally performed at a temperature in the range of 100 to 250° C., preferably 120 to 200° C. Generally, the reaction pressure is in the range of 15 to 450 psig, preferably in the range of 30 to 150 psig.

The feed preferably passes through the catalyst at a space velocity of in the range of 10 to 15,000 $h^{-1}$, more preferably in the range of 300 to 8,000 $h^{-1}$. Propylene conversion is generally 3 to 15%, and that of acetic acid 9 to 45%. Oxygen conversion can be up to 90%.

The acetoxylation reaction produces a mixture comprising allyl acetate, propylene, oxygen, acetic acid, water, allyl diacetate, carbon dioxide, and inert gases if used. Preferably the selectivity to allyl diacetate from propylene is no greater than 1%, for example, from 0.01 to 1%, more preferably from 0.1 to 0.5%.

The reaction mixture is distilled to produce a vapor stream comprising propylene, carbon dioxide, and oxygen, and a liquid stream comprising allyl acetate, water, acetic acid, acrolein, and allyl diacetate. Any conventional distillation may be used. The distillation column may have many suitable tray designs, for example, bubble cap trays, valve trays, sieve trays, random packing, or structured packing. The column used typically has 12 to 20 stages and operates at 100 to 300 psig with a reflux-to-distillate ratio of between 2 and 5. Preferably the vapor stream is recycled to the acetoxylation reaction. It may be necessary to remove at least a portion of the carbon dioxide present in the vapor stream, for example, with a potash (U.S. Pat. Nos. 3,970,713 and 4,409,396). There are various techniques to recycle the vapor stream. In one example, the vapor stream is fed to an acetic acid vaporizer (described in detail below) so that it is charged with the requisite quantity of acetic acid before it enters the reactor.

The liquid stream generally comprises 5 to 30 wt % allyl acetate, 2 to 20 wt % water, 10 to 70 wt % acetic acid, 0.01 to 2 wt % acrolein, and 0.01 to 5 wt % allyl diacetate.

The liquid stream is distilled to produce a lights stream comprising acrolein; a side draw comprising allyl acetate, acetic acid, and water; and a bottoms stream comprising acetic acid and allyl diacetate. Any conventional distillation may be used. The column used typically has 10 to 25 stages and operates at 20 to 75 psig with a reflux-to-feed ratio of between 2 and 5. Preferably the side draw is taken at a point below the entry point of the liquid stream to ensure that the side draw contains very low concentration of acrolein, for example, generally less than 0.01 wt %, more preferably less than 0.005 wt % acrolein. Typically the side draw contains 5 to 30 wt % allyl acetate, 10 to 70 wt % acetic acid, and less than 0.1 wt % allyl diacetate. The bottoms stream typically contains 80 to 99 wt % acetic acid, 0.5 to 10 wt % ally diacetate, and other heavy components.

The bottoms stream is vaporized in the acetic acid vaporizer. In addition to the bottoms stream, fresh acetic acid and acetic acid recovered from the allyl acetate hydrolysis and separation section (described below) are preferably fed to the acetic acid vaporizer. At least a portion of fresh propylene and recycled vapor stream is fed to the bottom portion of the acetic acid vaporizer to help to vaporize the acetic acid prior to its entry into the reactor. Typically the vaporizer is a trayed distillation column. The vaporizer is typically operated at a temperature of 80 to 140° C., preferably at 90 to 130° C. A heavies stream is obtained from the bottom portion of the vaporizer, which typically contains 2 to 20 wt % allyl diacetate, preferably 5 to 15 wt % allyl diacetate.

The process comprises reacting the side draw in the presence of acid catalyst to hydrolyze the allyl acetate to allyl alcohol and to generate a hydrolysis product mixture. The hydrolysis reaction is generally carried out at a temperature of 50 to 150° C. and under a pressure of 15 to 200 psig. An acid catalyst such as sulfuric acid, sulfonic acids, phosphoric acid, heteropoly acids, silica-aluminas, or an acidic ion-exchange resin may be used. Preferably a solid acidic catalyst is used. More preferably an acidic ion-exchange resin is used.

The hydrolysis product mixture is processed to separate allyl alcohol and acetic acid. The acetic acid is preferably recycled to the acetoxylation reaction. Typically the separation of allyl alcohol and acetic acid is carried out by azeotropic distillations. Suitable methods can be found in U.S. Pat. No. 4,743,707 and U.S. Pat. Appl. Pub. No. 2009/0166174, and references cited therein.

This invention removes heavy impurities such as allyl diacetate from the process streams without the need of using a decomposition reactor. Instead, the heavy impurities are efficiently separated using the acetic acid vaporizer.

Example 1

One proposed process for producing 50,000 metric tons of allyl alcohol per year according to this invention is shown in FIG. 1. Reactor 101 is charged with a catalyst as described in Example 3 of co-pending U.S. patent application Ser. No. 12/586,966, filed Sep. 30, 2009). Fresh propylene (containing 5 mol % propane) is fed to acetic acid vaporizer 105 via line 3. A vapor stream that is recycled from distillation column 102 containing propylene, propane, oxygen, argon, and carbon dioxide is fed to carbon dioxide removal section 106 via line 5 where 80% of carbon dioxide is removed via line 16. The rest of the vapor stream enters vaporizer 105 via line 15. Fresh propylene and the recycle vapor stream may be combined before they enter vaporizer 105. Fresh acetic acid enters vaporizer 105 via line 2. A recycle stream containing acetic acid, water, and allyl diacetate enters vaporizer 105 via line 12. The stream in line 12 may be combined with the fresh acetic acid in line 2 before they are fed to vaporizer 105. Vaporizer 105 is a column with 5 to 20 trays and is operated at 114° C. and 90 psig at the top. Vaporizer 105 has a liquid pump-around loop (not shown) that circulates and heats the fresh and recycled acetic acid. The vapor stream coming out of vaporizer 105 is mixed with fresh oxygen (containing 0.1 mole % argon) in line 1 and fed to acetoxylation reactor 101 via line 13. The acetoxylation reaction is conducted at 145° C. and 80 psig. The gas hourly space velocity is controlled at 2200 h$^{-1}$. The reaction mixture from the acetoxylation reactor is fed to distillation column 102 via line 4. Column 102 has 15 stages and operates at 200 psig with a reflux ratio of between 2 and 5. The acetoxylation reaction mixture enters column 102 at stage 10 from the top. Column 102 may also be equipped with a decanter for removal of excess water. The liquid stream from column 102, which contains acetic acid, allyl acetate, allyl diacetate, and acrolein, is fed to distillation column 103 via line 6. A vapor stream from column 102, which contains propylene, propane, oxygen, and argon, is recycled to acetic acid vaporizer 105 via line 5. The liquid stream from column 102, which contains acetic acid, allyl acetate, allyl diacetate, and acrolein, is fed to distillation column 103 via line 6. Column 103 has 15 stages and operates at about 35 psig. The liquid stream enters column 103 at stage 9 from the top. The reflux to feed ratio is about 3:1. A lights stream from column 103, which contains water and acrolein, is taken as overhead via line 7. A bottoms stream containing acetic acid and allyl diacetate exits column 103 via line 8. A vapor side draw containing allyl acetate, acetic acid, and water is taken from stage 13 from the top of column 103 via line 9 and is condensed and fed to hydrolysis and separation section 104. The details of section 104 are not shown. The hydrolysis of allyl acetate occurs in the presence of an acidic ion-exchange resin. The hydrolysis product is separated into allyl alcohol product (in line 10), and a recycle stream containing acetic acid and water (in line 11), which is combined with the bottoms stream in line 8 and recycled to vaporizer 105. A heavy residue containing allyl diacetate and acetic acid exits vaporizer 105 via line 14. The compositions and the flow rates of the streams are shown in Table 1.

TABLE 1

| Composition (Mole/h) | Stream | | | | | | | | |
|---|---|---|---|---|---|---|---|---|---|
| | 1 | 2 | 3 | 4 | 5 | 6 | 7 | 8 | 9 |
| Oxygen | 56.87 | | | 43.64 | 43.04 | | | | |
| Argon | 0.056 | | | 4.05 | 3.99 | | | | |
| Carbon Dioxide | | | | 1.96 | 1.94 | | | | |
| Propylene | | 130.13 | | 1807.23 | 1782.28 | | | | |
| Propane | | 6.53 | | 473.66 | 467.12 | | | | |
| Acrolein | | | | 0.63 | | 0.63 | 0.63 | | |
| Allyl alcohol | | | | | | | | | |
| Water | | | | 436.49 | | 436.48 | 3.26 | | 433.27 |
| Allyl Acetate | | | | 103.50 | | 103.50 | | | 103.50 |
| Allyl diacetate | | | | 0.52 | | 0.52 | | 0.53 | |
| Acetic Acid | | | 5.78 | 373.55 | | 373.55 | | 25.77 | 347.78 |
| Total (Kg/h) | 1790 | 5764 | 347 | 139358 | 97220 | 40777 | 94 | 1630 | 39051 |

| Composition (Mole/h) | Stream | | | | | | |
|---|---|---|---|---|---|---|---|
| | 10 | 11 | 12 | 13 | 14 | 15 | 16 |
| Oxygen | | | | 98.92 | | 43.04 | |
| Argon | | | | 4.05 | | 3.99 | |
| Carbon Dioxide | | | | 0.39 | | 1.93 | 1.55 |
| Propylene | | | | 1912.42 | | 1782.28 | |
| Propane | | | | 473.66 | | 467.12 | |
| Acrolein | | | | | | | |
| Allyl alcohol | 103.50 | | | | | | |
| Water | | 329.73 | 329.73 | 329.73 | | | |
| Allyl Acetate | | | | | | | |
| Allyl diacetate | | | 0.53 | | 0.53 | | |
| Acetic Acid | | 451.28 | 477.05 | 478.10 | 4.73 | | |
| Total (Kg/h) | 6011 | 33040 | 34670 | 139358 | 367 | 97151 | 68 |

We claim:

1. A process for producing allyl alcohol, comprising (a) reacting a feed comprising propylene, acetic acid, and oxygen to produce a reaction mixture; (b) distilling the reaction mixture to produce a vapor stream comprising propylene and a liquid stream comprising allyl acetate, acetic acid, acrolein, and allyl diacetate; (c) distilling the liquid stream to produce a lights stream comprising acrolein; a side draw comprising allyl acetate, acetic acid, and water; and a bottoms stream comprising acetic acid and allyl diacetate; (d) vaporizing the bottoms stream in an acetic acid vaporizer to remove a heavies stream comprising allyl diacetate; and (e) hydrolyzing the side draw to produce allyl alcohol.

2. The process of claim 1 wherein step (a) is performed in the presence of a palladium catalyst.

3. The process of claim 1 wherein step (a) is performed in the presence of a supported palladium catalyst.

4. The process of claim 1 wherein at least a portion of the vapor stream is fed to the acetic acid vaporizer.

5. The process of claim 1 wherein step (a) produces allyl diacetate from propylene with a molar selectivity of 0.01 to 1%.

6. The process of claim 1 wherein step (a) produces allyl diacetate from propylene with a molar selectivity of 0.1 to 0.5%.

7. The process of claim 1 wherein the bottoms stream comprises from 1 to 10 wt % allyl diacetate.

8. The process of claim 1 wherein the heavies stream comprises from 2 to 20 wt % allyl diacetate.

9. The process of claim 1 wherein the heavies stream comprises from 5 to 15 wt % allyl diacetate.

10. The process of claim 1 wherein the acetic acid vaporizer is a trayed distillation column.

11. The process of claim 1 wherein the acetic acid vaporizer is operated at an overhead temperature of 90 to 130° C.

12. The process of claim 1 wherein step (e) is performed in the presence of a solid acid catalyst.

13. The process of claim 12 wherein the solid acid catalyst is an ion-exchange resin.

* * * * *